(12) United States Patent
Nord et al.

(10) Patent No.: US 6,315,447 B1
(45) Date of Patent: Nov. 13, 2001

(54) VARIABLE COMPOSITION PHANTOM SIMULATING VARYING DEGREES OF BODY FAT FOR DUAL ENERGY X-RAY MACHINE CALIBRATION

(75) Inventors: Russell H. Nord, Fort Atkinson, WI (US); Colin G. Miller, Churchville, PA (US)

(73) Assignee: Bio-Imaging Technologies, Inc., West Trenton, NJ (US)

( * ) Notice: Subject to any disclaimer, the term of this patent is extended or adjusted under 35 U.S.C. 154(b) by 0 days.

(21) Appl. No.: 09/467,318

(22) Filed: Dec. 20, 1999

Related U.S. Application Data
(60) Provisional application No. 60/113,491, filed on Dec. 22, 1998.

(51) Int. Cl.[7] ........................................... G01D 18/00
(52) U.S. Cl. ........................ 378/207; 378/18; 378/51; 378/53; 378/56; 378/98.9
(58) Field of Search ............................. 378/51, 53, 54, 378/56, 98.9, 207, 18

(56) References Cited

U.S. PATENT DOCUMENTS

| | | | |
|---|---|---|---|
| 4,225,789 | * 9/1980 | Albrecht | 378/5 |
| 4,980,904 | * 12/1990 | Sones et al. | 378/207 |
| 5,123,037 | * 6/1992 | Picard et al. | 378/98.2 |
| 5,396,530 | * 3/1995 | Tsutsui et al. | 378/98.11 |
| 5,565,678 | * 10/1996 | Manian | 250/252.1 |
| 5,841,835 | * 11/1998 | Aufrichtig et al. | 378/207 |
| 5,844,965 | * 12/1998 | Galkin | 378/207 |
| 6,076,966 | * 6/2000 | Stueve | 378/207 |
| 6,148,057 | * 11/2000 | Urchuk et al. | 378/18 |
| 6,173,038 | * 1/2001 | Siffert et al. | 378/56 |

\* cited by examiner

Primary Examiner—Robert H. Kim
Assistant Examiner—Allen C. Ho
(74) Attorney, Agent, or Firm—Quarles & Brady LLP

(57) ABSTRACT

Disclosed herein is a phantom for calibrating dual energy x-ray equipment for body fat measurements. In particular, the present invention provides a limited number of calibrated plates of materials simulating different body fat percentages. By combining the plates, a range of simulated body fat compositions may be precisely obtained. The plates may be of arbitrary size to provide a simulation over a broad area and may include a high density end cap for triggering an automatic region of interest detection for certain scanner systems.

17 Claims, 1 Drawing Sheet

US 6,315,447 B1

VARIABLE COMPOSITION PHANTOM SIMULATING VARYING DEGREES OF BODY FAT FOR DUAL ENERGY X-RAY MACHINE CALIBRATION

CROSS-REFERENCE TO RELATED APPLICATIONS

This application claims the benefit of provisional application Ser. No. 60/113,491, filed Dec. 22, 1998.

STATEMENT REGARDING FEDERALLY SPONSORED RESEARCH OR DEVELOPMENT

BACKGROUND OF THE INVENTION

The present invention relates to calibration phantoms for x-ray machines and the like and, in particular, to a phantom providing calibration of dual energy x-ray equipment for percent body fat measurements.

The absorption of x-rays by material is dependent on two independent absorption mechanisms: Compton scattering and the photoelectric absorption. Each of these absorption mechanisms differs in relative contribution for different materials. Further, the amount of absorption by each of these mechanisms is dependent on the energy of the x-rays. Measurements of the attenuation of a body at two x-ray energies (generally corresponding to different x-ray frequencies) can therefore reveal information about the relative contribution of Compton scattering and the photoelectric absorption by materials of the body and thus can reveal information about the constituent materials of the body.

One important use of dual energy measurement is in determining relative proportions of bone and soft tissue in a patient providing information about the patients bone mass. Lunar Corporation, the assignee of the present application, manufactures a number of dual energy x-ray machines suitable for this purpose as described in the following U.S. patents hereby incorporated by reference: U.S. Pat. Nos. 5,253,282; 5,228,068; 5,287,546; 5,291,537; 5,305,368; 5,306,306; 5,408,439; 5,485,492; 5,509,042; 5,533,080; 5,533,084; 5,577,089 and 5,673,298.

If the basis materials are chosen to be tissue and fat instead of tissue and bone, the same techniques may be used to provide a measurement of percentage body fat as may be useful in the investigation of drugs and in the study of wasting diseases.

In either of these applications, it is important that repeatable quantitative results be produced. For this reason, the entire patient may be scanned so as to eliminate variation caused by change in measurement regions for different patients or the location of the measurement region between measurements of a single patient. Further, the machine must be calibrated both to prevent drifting of the measurements of a single machine over time and, in the case where multiple machines are used in a study, to ensure consistency among results. Critical to this calibration is that the machines produce identical readings for the same patient at a given time regardless of the patient's body fat. Given that a total body scan will typically be used, it is preferable that the calibration process reflect measurements over a substantial area on the machine.

What is needed is a simple and reliable phantom that allows accurate calibration of dual energy equipment for body fat measurement under these constraints.

BRIEF SUMMARY OF THE INVENTION

The present invention provides a simple yet accurate phantom for calibrating dual energy x-ray equipment for body fat measurements. In particular, the present invention provides a limited number of standard plates of materials simulating different body fat percentages. By combining the plates, a range of body fat percentages may be precisely obtained. The plates may be of arbitrary size to provide a simulation over a broad area and may include a high density end cap for triggering an automatic region of interest detection for certain scanner systems.

In particular, the present invention is a modular body fat phantom for calibrating body fat percentage measurements made by a dual energy x-ray attenuation measurement device. The body fat phantom includes a first calibrated plate made of a first basis material having a first high energy x-ray attenuation value and a first low energy x-ray attenuation value. The phantom also includes a second calibrated plate made of a second basis material having a second high energy x-ray attenuation value and a second low energy x-ray attenuation value. The second set of x-ray attenuation values is different from the second set of x-ray attenuation values. The two plates may be stacked together to define a known simulated body fat composition.

Preferably, stacking the first and second calibrated plates together defines a simulated body fat composition less than that of the first calibrated plate alone.

In one aspect of the invention, the body fat phantom can also include a third calibrated plate made of a third basis material having a third set of high and low energy x-ray attention values different from both the first and second sets x-ray attenuation values. The calibrated plates may be stacked together to define a second known simulated body fat composition. Preferably, stacking the first, second and third calibrated plates together defines a simulated body fat composition less than that of the first and second calibrated plates.

In another aspect, the body fat phantom has a plurality of first, second and third calibrated plates stackable in different combinations to define various known simulated body fat compositions.

In another aspect, the modular body fat phantom includes a high density end cap positionable next to a first end of the calibrated plates. The end cap is used for for triggering an automatic region of interest detection in certain known attenuation measurement devices.

Thus, the present invention provides a modular body fat phantom comprised of a number of calibrated plates of various materials simulating different percentages of body fat when scanned by dual energy x-ray measurement equipment. The plates can be configured into various stacks having different combinations of plates to provide a phantom of variable simulated body fat compositions for calibrating dual energy x-ray equipment at various attenuation levels.

These and still other advantages of the present invention will be apparent from the description of the preferred embodiments which follow.

DETAILED DESCRIPTION OF THE INVENTION

Figure 1:
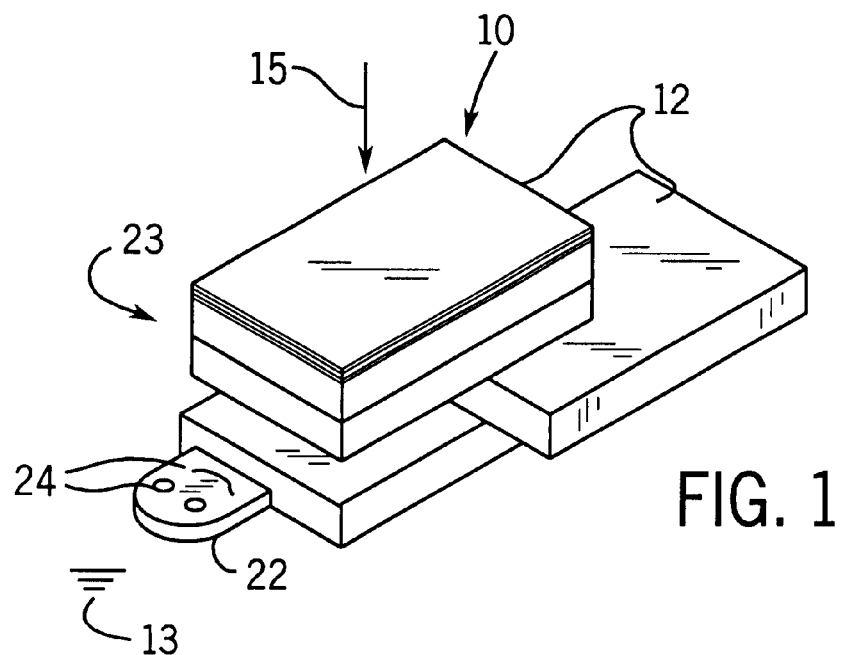
FIG. 1 is a perspective view of the plates of the present invention as assembled into a phantom with one plate shifted to the side to show their separable nature.

Referring now to FIG. 1, a phantom 10 comprises a plurality of rectangular plates 12 positionable on a table 13 of a dual energy x-ray machine (not shown) to intercept x-rays along an axis 15.

Each of the plates 12 present a predetermined thickness measured along the axis 15 over a rectangular area of twenty by twenty-eight centimeters. The material and particular thickness of the plates 12, however, differs among the plates 12. Specifically, four of the plates 12 are comprised of clear acrylic 16 having a thickness of approximately 2.875 (2⅞) inches. Two of the plates 12 are comprised of polyvinylchloride 18 having a thickness of 0.060 inches and four of the plates 12 are comprised of vinyl 20 having a thickness of 0.015 inches. The polyvinylchloride and vinyl may be obtained from Vycom of Moosic, Pa.

Generally the addition of the polyvinylchloride 18 and the vinyl 20 reduce the simulated percent body fat of the phantom provided by the acrylic 16.

Referring now to Table 1, the plates 12 may be combined into five configurations A through E presenting different simulated percent body fats to the dual energy x-ray unit.

TABLE 1

| Configuration | Plates of Clear Acrylic | Plates of Gray PVC | Sheets of White Vinyl | VCP-03% Fat |
|---|---|---|---|---|
| A | A1-A4 | P1 | 0 | 42 |
| B | A1-A4 | P1 | V1 and V2 | 35 |
| C | A1-A4 | P1 and P2 | 0 | 25 |
| D | A1-A4 | P1 and P2 | V1 and V2 | 18 |
| E | A1-A4 | P1 and P4 | V1 through V4 | 12 |

Each of the sheets 12 is given a number with the acrylic sheets being labeled A1 through A4, the polyvinylchloride sheets being labeled P1 through P2, and the vinyl sheets being labeled V1 through V4. Thus as shown, a range of percent body fats from 12 to 42 may be readily assimilated with the present invention.

Referring again to FIGS. 1 and 2, an aluminum disk 22 representing a highly x-ray attenuating medium along axis 15 may be placed abutting a front edge 23 of the stack plates 12. The disk may be approximately 2⅞ inches in diameter and ¼ inch thick with a flattened circumference along one tangent at the lower edge to allow it to lay flat on the patient table 13 and abut the bottom plate 12 at the lower edge. Orienting indicia 24 may be embossed on or bored through the front surface reflecting its nature as a simulation of a patient head such as may trigger automatic scan protocols in certain dual energy densitometers when used for total body imaging. Bone simulating members (not shown) may be embedded into, or disposed within suitable channels in, one or more of the blocks. These members are preferably made of variously sized aluminum strips approximating the x-ray attenuation characteristics of some or all of a human skeleton.

Figure 2:
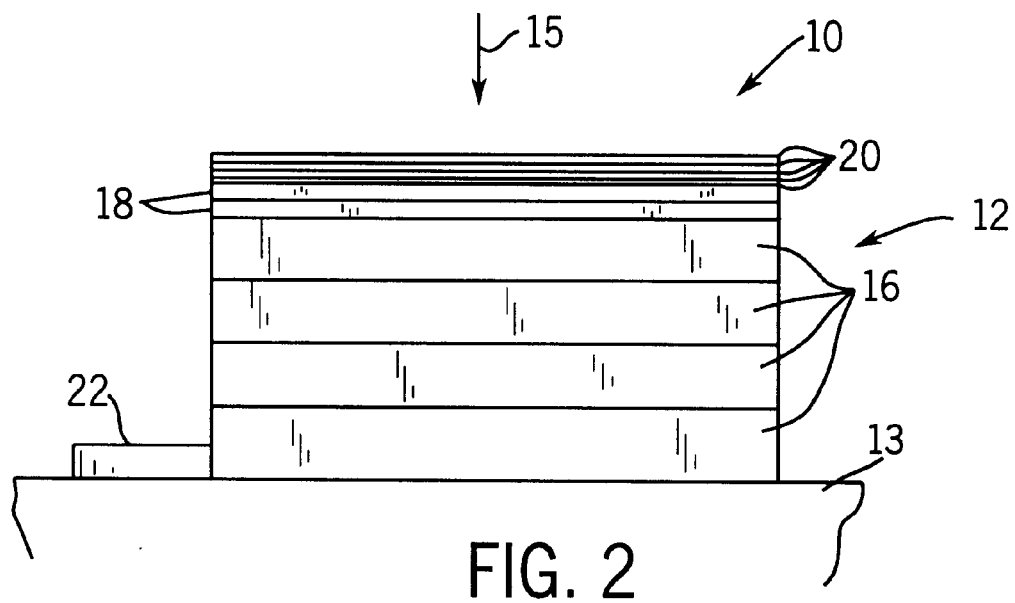
FIG. 2 is a side elevational view of the phantom assembled for minimum percent body fat measurement.

In use, the patient pad, if any, can be removed from the scanner table or kept in place, and four of the acrylic plates are placed on the table vertically aligned with each other as shown in FIG. 2 with the aluminum disk 22 abutting a front edge of the stack near the head position of the table 13. The PVC sheet P1 is then placed on top of this stack to make configuration A shown in Table 1. A scan of this configuration may be performed then repeated and the results averaged. Next configurations B through E may be adopted by adding or removing PVC or vinyl sheets from the top of the acrylic stack as indicated in Table 1. The order of the sheets 12 in the stack is not important but it is important that correct sheets be used according to their numbers to avoid variation in measurements caused by manufacturing differences in the thinner sheets.

The present invention may include other aspects not specifically delineated in the aforementioned preferred embodiments. For example, any number of plates and sheets may be used to practice the present invention. Thus, the above in no way is intended to limit the scope of the invention. Accordingly, in order to apprise the public of the full scope of the present invention, reference must be made to the following claims.

We claim:

1. A modular body fat phantom for calibrating body fat percentage measurements made by a dual energy x-ray attenuation measurement device, the body fat phantom comprising:
    a first calibrated plate made of a first basis material having a first high energy x-ray attenuation value and a first low energy x-ray attenuation value; and
    a second calibrated plate made of a second basis material having a second high energy x-ray attenuation value and a second low energy x-ray attenuation value, wherein the second set of high and low energy x-ray attenuation values is different from the first set of high and low energy x-ray attenuation values;
    wherein the first and second calibrated plates may be stacked together to define a first known simulated body fat composition.

2. The modular body fat phantom of claim 1, comprising a plurality of first and second calibrated plates stackable in different combinations to define various known simulated body fat compositions.

3. The modular body fat phantom of claim 1, wherein the first and second calibrated plates have a rectangular planar geometry.

4. The modular body fat phantom of claim 3, wherein the area of the first and second calibrated plates is approximately 20 square centimeters.

5. The modular body fat phantom of claim 3, wherein the first and second calibrated plates have different thicknesses.

6. The modular body fat phantom of claim 1, wherein the first basis material is acrylic and the second basis material is a vinyl-based substance.

7. The modular body fat phantom of claim 1, wherein stacking the first and second calibrated plates together defines a simulated body fat composition less than that of the first calibrated plate alone.

8. The modular body fat phantom of claim 1, further comprising a high density end cap positionable proximate a first end of the first and second calibrated plates for triggering an automatic region of interest detection in the measurement device.

9. The modular body fat phantom of claim 8, wherein the end cap is aluminum.

10. The modular body fat phantom of claim 1, further comprising a third calibrated plate made of a third basis material having a third set of high and low energy x-ray attention values different from both the first and the second sets of high and low energy x-ray attenuation values, wherein the first, second and third calibrated plates may be stacked together to define a second known simulated body fat composition.

11. The modular body fat phantom of claim 10, comprising a plurality of first, second and third calibrated plates stackable in different combinations to define various known simulated body fat compositions.

12. The modular body fat phantom of claim 10, wherein the first, second and third calibrated plates all have different thicknesses.

13. The modular body fat phantom of claim 10, wherein the first basis material is acrylic, the second basis material is vinyl and the third basis material is polyvinylchloride.

14. The modular body fat phantom of claim 10, wherein stacking the first, second and third calibrated plates together defines a simulated body fat composition less than that of the first and second calibrated plates.

15. The modular body fat phantom of claim 10, further comprising a high density end cap positionable proximate a first end of the first, second and third calibrated plates for triggering an automatic region of interest detection in the measurement device.

16. The modular body fat phantom of claim 1, further comprising an skeletal bone simulating member within one of the calibrated plates, simulating the attenuation of x-rays by human bone.

17. A modular body fat phantom comprising a plurality of plates of at least three different materials simulating different percentages of body fat when scanned by dual energy x-rays, the plates removably stackable into stacks having different combinations of plates to provide a phantom of varying body fat simulation.

* * * * *